(12) United States Patent
Midorikawa et al.

(10) Patent No.: US 10,857,374 B2
(45) Date of Patent: Dec. 8, 2020

(54) EXCITATION COIL AND COIL UNIT

(71) Applicant: Teijin Pharma Limited, Tokyo (JP)

(72) Inventors: Masamichi Midorikawa, Tokyo (JP);
Takamitsu Okayama, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 367 days.

(21) Appl. No.: 15/516,735

(22) PCT Filed: Dec. 8, 2015

(86) PCT No.: PCT/JP2015/084362
§ 371 (c)(1),
(2) Date: Apr. 4, 2017

(87) PCT Pub. No.: WO2016/093213
PCT Pub. Date: Jun. 16, 2016

(65) Prior Publication Data
US 2017/0291038 A1    Oct. 12, 2017

(30) Foreign Application Priority Data
Dec. 9, 2014  (JP) .................................. 2014-248651

(51) Int. Cl.
*A61N 2/02* (2006.01)
*A61N 1/40* (2006.01)
*A61N 1/04* (2006.01)
*A61N 2/00* (2006.01)

(52) U.S. Cl.
CPC .............. *A61N 2/02* (2013.01); *A61N 1/0456* (2013.01); *A61N 1/0484* (2013.01); *A61N 1/40* (2013.01); *A61N 2/006* (2013.01)

(58) Field of Classification Search
CPC ........ A61N 2/02; A61N 1/0456; A61N 1/0484; A61N 2/006; A61N 1/40
See application file for complete search history.

(56) References Cited

U.S. PATENT DOCUMENTS

| 8,568,287 B2 | 10/2013 | Saitoh |
| 2008/0281318 A1 | 11/2008 | Herbette et al. |
| 2009/0187062 A1 | 7/2009 | Saitoh |

(Continued)

FOREIGN PATENT DOCUMENTS

| JP | 05-055062 A | 3/1993 |
| JP | 2009-218321 A | 9/2009 |

(Continued)

OTHER PUBLICATIONS

International Search Report for PCT/JP2015/084362 dated Mar. 1, 2016 [PCT/ISA/210].

(Continued)

*Primary Examiner* — Kaylee R Wilson
(74) *Attorney, Agent, or Firm* — Sughrue Mion, PLLC

(57) ABSTRACT

The purpose of the present invention is to provide a miniaturized excitation coil with increased safety as an excitation coil used in magnetic stimulation therapy. The present invention provides an excitation coil having a spiral conductive wire part that generates a magnetic field, characterized by the conductive wire end faces of the spiral conductive wire part being parallel with respect to the central axis of the excitation coil.

4 Claims, 4 Drawing Sheets

(56) References Cited

U.S. PATENT DOCUMENTS

| | | | |
|---|---|---|---|
| 2013/0150653 A1* | 6/2013 | Borsody | A61N 2/006 600/13 |
| 2014/0235928 A1* | 8/2014 | Zangen | A61N 2/02 600/14 |
| 2015/0196772 A1* | 7/2015 | Ghiron | A61N 2/006 600/14 |
| 2016/0030763 A1 | 2/2016 | Midorikawa et al. | |

FOREIGN PATENT DOCUMENTS

| JP | 2010-531204 A | | 9/2010 |
|---|---|---|---|
| JP | 2012-125546 A | | 7/2012 |
| JP | 2012125546 A | * | 7/2012 |
| JP | 5530783 B2 | | 6/2014 |
| WO | 2007/123147 A1 | | 11/2007 |
| WO | 2014/163020 A1 | | 10/2014 |

OTHER PUBLICATIONS

Written Opinion for PCT/JP2015/084362 dated Mar. 1, 2016 [PCT/ISA/237].

Communication, dated May 15, 2018, issued by the Japanese Patent Office in counterpart Japanese Application No. 2016-563677.

Communication, dated Jul. 31, 2018, issued by the Japanese Patent Office in counterpart Japanese Patent Application No. 2016-563677.

* cited by examiner

[Fig. 1]
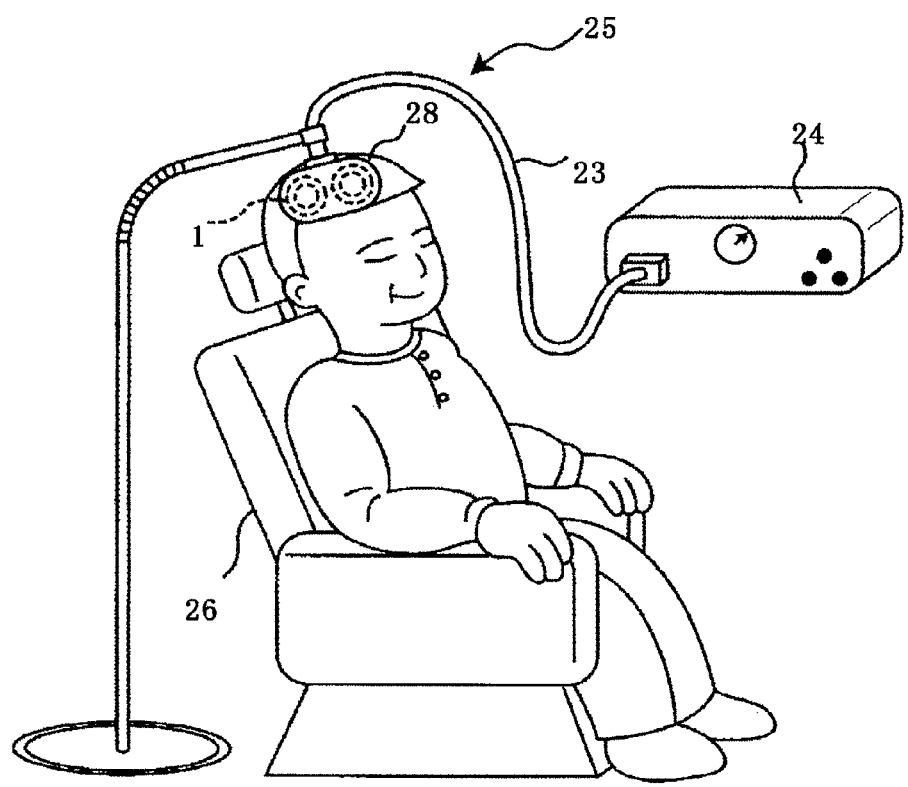

[Fig. 2]
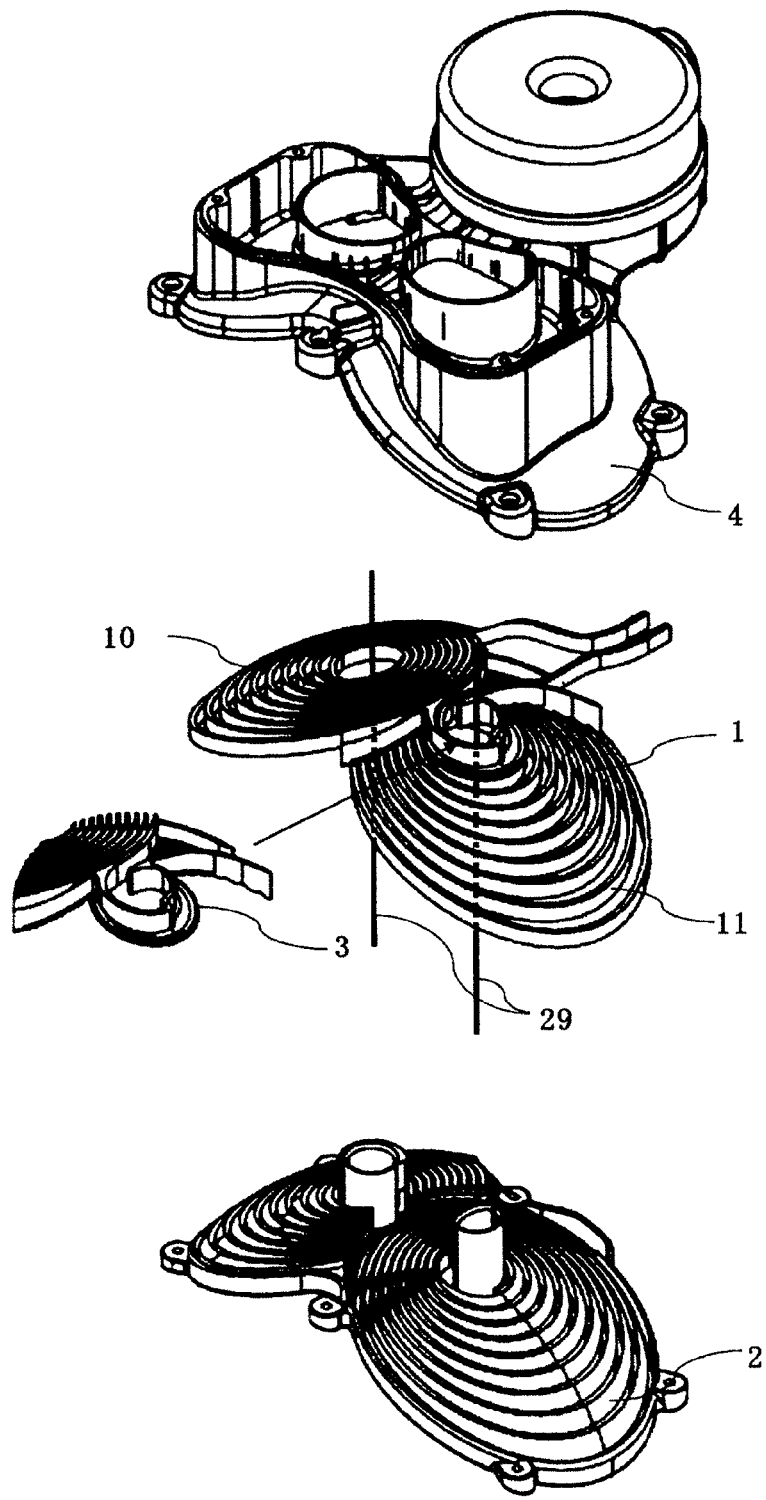

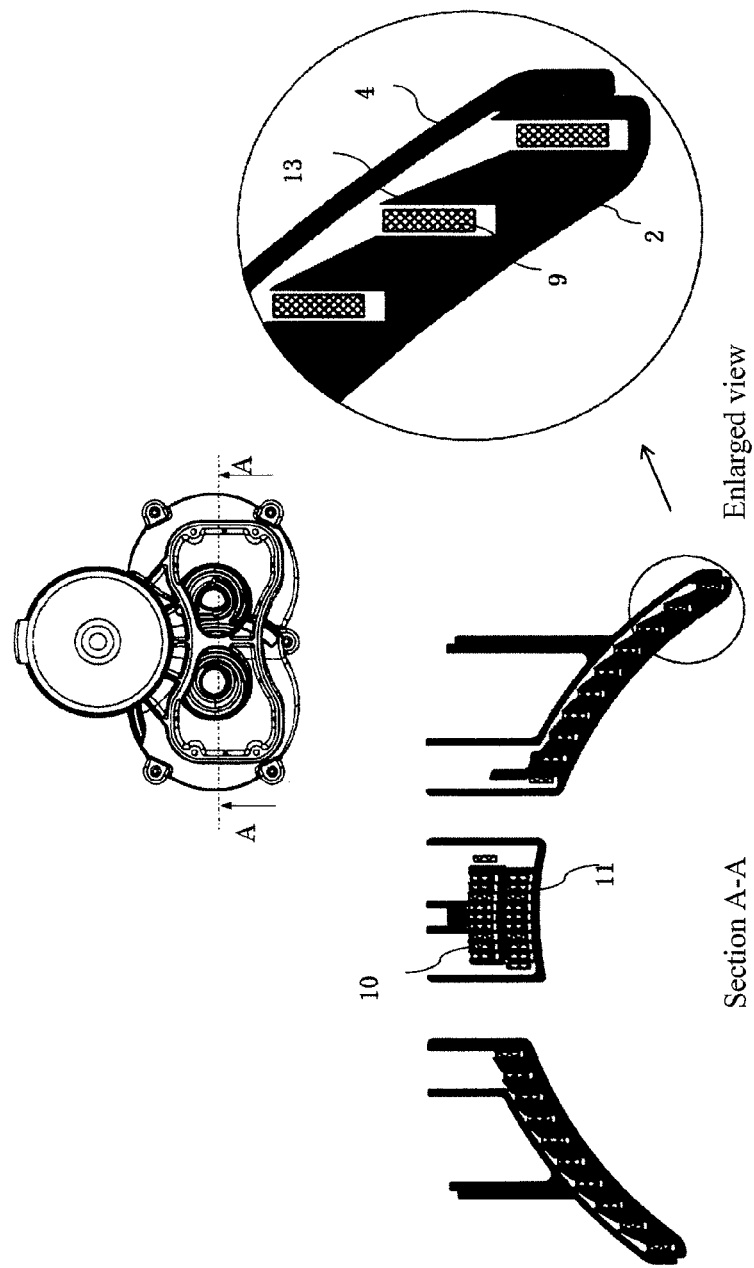

[Fig. 4]
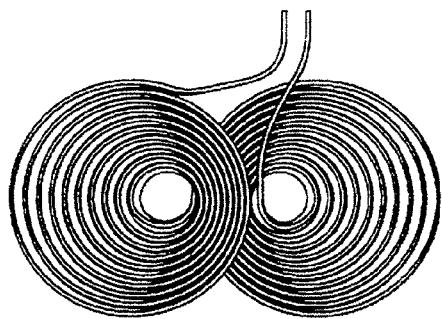 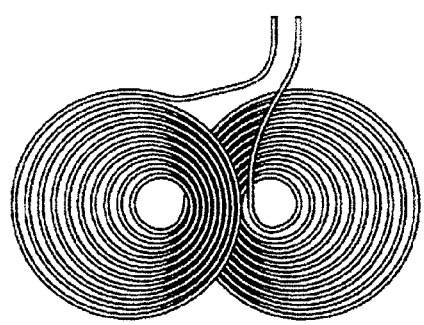
(a-1) (a-2)
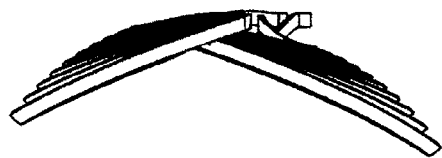 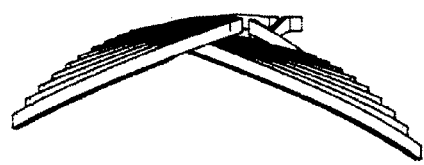
(b-1) (b-2)
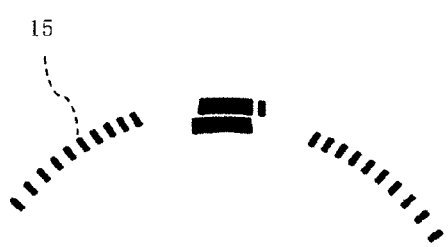 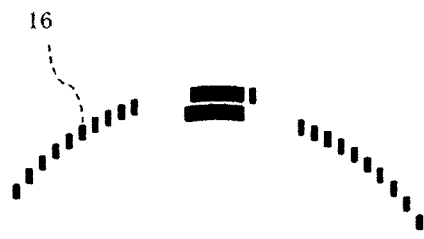
(c-1) (c-2)

EXCITATION COIL AND COIL UNIT

CROSS REFERENCE TO RELATED APPLICATIONS

This application is a National Stage of International Application No. PCT/JP2015/084362 filed Dec. 8, 2015, claiming priority based on Japanese Patent Application No. 2014-248651 filed Dec. 9, 2014, the contents of all of which are incorporated herein by reference in their entirety.

TECHNICAL FIELD

The present invention relates to an excitation coil and a coil unit, and specifically to an excitation coil and a coil unit for use in transcranial magnetic stimulation system.

BACKGROUND ART

The repetitive transcranial magnetic stimulation (rTMS) is a method of treatment that enables to treat, relieve and improve symptoms of neurological disorder such as post-stroke pain, depression and Alzheimer's disease by noninvasively applying magnetic stimulation to a specific region of the brain such as an intracerebral nerve.

In the transcranial magnetic stimulation therapy, a magnetism generation means such as an excitation coil is disposed in a specific position on a surface of scalp of a patient, and magnetic stimulation is applied to a specific part of a brain of the patient by the magnetism generating means. As a specific method, PTL 1 discloses that stimulation is applied to intracerebral nerve just under a coil unit disposed on the surface of the scalp of the patient by passing a current through the coil unit to locally produce a minute pulse magnetic field, thereby generating an eddy current in the cranium by using the principle of electromagnetic induction.

Various types of excitation coil are used for use in the transcranial magnetic stimulation therapy. While the excitation coil shaped in a figure of eight is common as shown in PTL 1 and PTL 2, those with mountain shape or circle shape also exist. However, since usual excitation coils are large, it may be difficult to operate the excitation coils, and operability may be poor at the time of prescribing and treating.

Moreover, as a method of forming curved coils, PTL 3 and PTL 4 are cited. These curved surface shape spiral coils are realized by attaching a coil on a plane sheet to bend the coil along with the plane sheet, or by pressing, by a curved surface press machine, the spiral coils constituted in a plane shape in a previous process, thereby bending the coils.

CITATION LIST

Patent Literature

[PTL 1]
  WO 2007/123147
[PTL 2]
  WO 2014/163020
[PTL 3]
  Japanese Unexamined Patent Application Publication No. 2009-218321
[PTL 4]
  Japanese Patent No. 5530783

SUMMARY OF INVENTION

Technical Problem

The purpose of the present invention is to provide a miniaturized excitation coil as an excitation coil used in magnetic stimulation therapy.

Solution to Problem

The present invention is an excitation coil comprising a spiral conductive wire portion generating a magnetic field, wherein a side of a rectangle or an axis of an ellipse of a conductive wire end face is parallel to a central axis, wherein the conductive wire end face is a cross-section formed when the conductive wire of the spiral conductive wire portion is cut perpendicularly to a longitudinal direction, and the central axis is a center of a spiral of the spiral conductive wire portion of the excitation coil.

In addition, the present invention is preferably the excitation coil, wherein the excitation coil is provided in a coil case comprising a coil upper case and a coil lower case, wherein the coil lower case has a groove portion, and the spiral conductive wire portion of the excitation coil is fitted in the groove portion.

Further, in the present invention, the groove portion is preferably configured to be parallel to the central axis of the excitation coil.

Further, in the present invention, a coil bottom face of the excitation coil is preferably formed in a curved surface shape.

Advantageous Effects of Invention

The excitation coil according to the present invention is capable of contributing to miniaturization of the excitation coil, since an end face of a conductive wire is configured to be parallel to the central axis of the excitation coil.

BRIEF DESCRIPTION OF DRAWINGS

FIG. 1 is a schematic view of a transcranial magnetic stimulation system.

FIG. 2 is an exploded view illustrating an example of an excitation coil and a coil case of the present invention.

FIG. 3 is a cross-sectional view of the excitation coil and the coil case of the present invention.

FIG. 4 is a top view, a side view, and a cross-sectional view of the excitation coil of the present invention.

DESCRIPTION OF EMBODIMENTS

Hereinafter, a transcranial magnetic stimulation system according to embodiments of the present invention will be described with reference to the attached drawings. Although a transcranial magnetic stimulation system suitable for use in medical fields such as post-stroke pain will be described in the following embodiments, the present invention is also applicable to medical fields such as neurosurgery of other pains, depression, Alzheimer's disease and the like and psychiatry and the like.

In addition, although the terms (for example, "upper surface", "lower surface", etc.) describing a direction or a position are used for the sake of convenience in the following description, those are aimed at facilitating the understanding of the present invention, and the technical scope of the present invention is not limited by the meanings of those terms. Moreover, the following description is only an illustration of one embodiment of the present invention, and does not intend to restrict the present invention, articles to which the present invention is applied, or use thereof.

In FIG. 1, a transcranial magnetic stimulation system is schematically shown. The cranial magnetic stimulation system 25 (hereinafter simply referred to as "magnetic stimulation system 1") has the excitation coil 1 (magnetic field generation means) electrically connected to the coil drive power supply 24 through the cable 23. The coil drive power supply 24 is connected to an external power supply, etc., and has the function to supply electric power to the excitation coil 1. A patient fixes one's head while, for example, sitting down on the chair 26 for the medical treatment, and the excitation coil 1 is disposed in the specific position useful for the medical treatment on the surface of the scalp. The treatments, etc. are performed by applying a magnetic stimulation of a predetermined intensity to the intracerebral nerve of the patient by the excitation coil 1 disposed in the specific position. The coil drive power supply 24 controls supply of the current pulse to the excitation coil 1, and conventionally known various types can be used. An operator can perform ON/OFF operation of the coil drive power supply 24 and a setting, etc. of an intensity and a pulse shape of a current pulse for determining an intensity and a cycle of the magnetic stimulation.

The excitation coil 1 is incorporated into the coil cases 2 and 4, and further accommodated in the coil unit 28. In FIG. 2, the coil case is divided into a coil upper case and a coil lower case. The coil case accommodates inside thereof the excitation coil 1. The coil unit 28 is provided inside thereof with the coil case 2, and includes peripheral mechanisms such as a mechanism for guiding a conductive wire connected from the excitation coil 1 to the coil drive power supply 24, a mechanism for cooling the coil, a temperature sensor of the excitation coil, a structure for incorporating the coil cooling mechanism, etc. A lower surface (i.e. a surface facing to the scalp surface of the patient) of the coil unit is formed in a concave curved surface shape corresponding to the head shape of the patient. Thus, the coil unit can be smoothly moved along the head surface of the patient. In addition, top view shape (shape of the coil unit when the whole coil unit is viewed from the bottom) of a coil unit may be elliptical including a long circle shape and an oval shape, or an egg shape.

In the medical institution, an optimal coil position and an posture of the excitation coil 1, in which neuropathic pain of a patient can be reduced most are determined at the time of primary care of the patient by using equipment designated for positioning. The optimal position and the posture of the excitation coil 1 can be easily reproduced from the next medical treatment by a method in which, for example, a marking for positioning is formed on or in the head surface of the patient.

In FIG. 2, the exploded view of the excitation coil 1 and the coil cases 2 and 4 are shown, and in FIG. 3, the cross-sectional view of the excitation coil 1 and the coil cases 2 and 4 are shown. In the medical treatment coil, the excitation coil 1 is wound in the shape of a spherical figure of eight for fitting to the head shape. The excitation coil 1 is constituted by spiral conductive wire portions, where the excitation coil is composed of two spiral conductive wire portions in the figs. In addition, although in the figs, the coil shaped in the spherical figure of eight is shown, the coil may also be shaped in a curved figure of eight. A spherical surface coil means a coil in which the bottom face of the coil is in a curved state like a portion of a spherical surface when the coil is put on a plane, and includes a coil having a spherical bottom face formed by winding the conductive wire and changing gradually the height of the wound conductive wire on each turn as shown in the fig. A curved surface coil also means a coil in which the bottom face takes a curved surface when the coil is put on a plane, and a spherical coil is a kind of curved coils.

In order to fix the wound conductive wire (spiral conductive wire portion) in the shape of a predetermined design value, it is desirable that the coil cases 2 and 4 accommodating the excitation coil 1 have the coil lower case 2 provided with the groove portion 13 arranged in advance around the coil central axis 29 and parallel to the coil central axis 29 and the coil upper case 4 provided with the installation portion for a cooling fan. The coil central axis 29 is a portion of the axis which is the center of the spiral in the spiral conductive wire portion of the coil, and it is perpendicular to a plane on which the coil is placed. A spacer 3 is provided in the portion where each of circular coils overlaps in the coil shaped in a figure of eight.

The excitation coil 1 shown in FIG. 2 is composed of two loops 10 and 11 (spiral conductive wire portions), in which the conductive wire 9 is wound to be shaped in the spherical figure of eight. In the spiral coil shaped in the spherical figure of eight, an induced current density becomes the maximum directly under a point corresponding to the intersection of the loops, and it is possible to give a localized stimulus. The loops 10 and 11 are held to mutually overlap the densely wound portions where intervals of the conductive wire 9 become narrow. The overlapped portions of the two loops 10 and 11 are separated by the spacer 3, by which the insulation is secured.

In FIG. 4, cross-sectional structures of the wound excitation coil 1 are shown. These show a top view (a-1), a side view (b-1), and a cross-sectional view (c-1) of the excitation coil in the conventional technology, and in contrast with the above, a top view (a-2), a side view (b-2), and a cross-sectional view (c-2) of the excitation coil in the present invention.

In PTLs 3 and 4, a spiral coil is configured to be curved surface shape (including spherical shape) after attaching the coil conductive wire on a sheet member. As the method therefor, the excitation coil is formed, for example, in the shape of a figure of eight and in a planar shape in the previous step before forming it in the curved surface shape. Next, the formed planar excitation coil, for example, is attached on a sheet (not shown) and the sheet to which the excitation coil is attached is inserted in an injection mold (not shown) having a curved surface shape for molding the coil in the curved surface shape and injected with a resin or similarly a curved surface sheet (not shown) to which the excitation coil 1 is attached is placed in a curved surface mold (not shown) and pressed, and thus the curved surface coil is produced. In this case, the conductive wire end face 15 of the excitation coil 1 follows the curved surface of each of the mold, and the end face is obliquely arranged. Here, the end face means a cross-section formed when the conductive wire of the excitation coil 1 is cut perpendicularly to the longitudinal direction. Moreover, the excitation coil is formed in a shape of a figure of eight and in a planar shape, and then this excitation coil shaped in a figure of eight is pressed against a curved surface shape manufacturing jig to follow its shape, and thus the curved surface shape excitation coil can be obtained. As described above, since the conductive wire end face 15 of the excitation coil follows the curved surface in the curved surface shape spiral coil based on the conventional technology, the end face is obliquely arranged, so that the lower part of the end face results in being made inwardly oblique ((a-1), (b-1), (c-1)). Since the groove portion 13 of the coil lower case 2 for fitting the conductive wire 9 is parallel to the coil central axis 29, in order to fit, in the coil lower case 2, such a conductive wire 9 wound in the spherical eccentric shape, the spiral coil by the conventional technology requires a coil lower case 2 with a wide groove. This configuration results in causing the upsizing of the coil unit.

Therefore, in the present invention, the whole coil is deformed to the curved surface shape (including the spherical shape) keeping the side or the axis of the conductive wire end face 16 parallel to the central axis ((a-2), (b-2), (c-2)). With this configuration, the conductive wire end face 16 can be fitted, parallel to the coil center axis 29, in the groove portion 13 provided in the coil lower case 2 shown in FIG. 3. Note that, the conductive wire end face in the present invention does not include a circular shape but includes a rectangular or elliptical shape. In the present invention, the terms rectangular or elliptical may be approximately rectangular or approximately elliptical.

Thus, the bottom face of the coil lower case 2 is not extended more than needed, by which the coil unit can be miniaturized. Note that in the present invention, being parallel denotes that it may be approximately parallel to the coil central axis 29. Moreover, even if it is not approximately parallel, the coil unit can be miniaturized by erecting the end face of the coil, in other word by arranging the side of the rectangle or the elliptical axis of the end face of the coil closer to parallel to the central axis of the coil and by thus decreasing the bottom face area. It is desirable that the portion of the end face to be arranged closer to approximately parallel or parallel is a long side when it is a rectangle or a long axis when it is an ellipse.

Although the embodiment having the groove portion 13 in the coil lower case 2 is shown in the above embodiment, even for a coil case without having the groove portion 13, the coil can be miniaturized by arranging the conductive wire end face of the coil parallel to the coil central axis 29 so as to decrease the bottom face area.

Moreover, although the embodiment of the curved surface (including spherical) eccentric coil shaped in a figure of eight is shown in the above, a shape of the coil in the present invention may be a single or a multiple concentric or eccentric shape, or an angular form etc., and a curved surface (including spherical) or a planar shape. The planar coil denotes the coil in which the coil bottom face is planar when the coil is put on a plane. Such coils can also be miniaturized by erecting the conductive wire end face and decreases the bottom face area.

REFERENCE SIGNS LIST

1 excitation coil
2 coil lower case
3 spacer
4 coil upper case
23 cable
9 conductive wire
10, 11 loop
13 groove portion
15, 16 end face of an excitation coil
24 coil driving power supply
25 transcranial magnetic stimulation
26 chair
28 coil unit
29 coil central axis

The invention claimed is:

1. An excitation coil shaped in a figure of eight, the excitation coil comprising:
    a first spiral conductive wire portion and a second spiral conductive wire portion that are configured to generate a magnetic field, wherein the first spiral conductive wire portion and the second spiral conductive wire portion respectively correspond to two geometric portions forming the figure of eight of the excitation coil and have central axes, respectively,
    wherein a side of a rectangle or an axis of an ellipse of a first conductive wire end face of the first spiral conductive wire portion is parallel to each of the central axes,
    wherein a side of a rectangle or an axis of an ellipse of a second conductive wire end face of the second spiral conductive wire portion is parallel to each of the central axes,
    wherein each of the first conductive wire end face and the second conductive wire end face is a cross-section formed when a conductive wire of each of the first spiral conductive wire portion and the second, spiral conductive wire portion, respectively, is cut perpendicularly to a longitudinal direction of the conductive wire,
    wherein each of the central axes is at a center of a spiral of the first spiral conductive wire portion and the second spiral conductive wire portion, respectively, and is perpendicular to a plane on which the excitation coil is placed, and
    wherein a coil bottom face of the excitation coil is formed in a curved surface shape.

2. The excitation coil according to claim 1, wherein a cross-section of the first spiral conductive wire portion comprises a first plurality of conductive wire end faces which are arranged to be staggered downward while being vertically oriented, the first conductive wire end face being one of the first plurality of conductive wire end faces, and
    a cross-section of the second spiral conductive wire portion comprises a second plurality of conductive wire end faces which are arranged to be staggered downward opposite to the first plurality of conductive wire end faces, while being vertically oriented, the second conductive wire end face being one of the second plurality of conductive wire end faces.

3. An excitation coil unit comprising:
    the excitation coil according to claim 1; and
    a coil case comprising a coil upper case and a coil lower case,
    wherein the coil lower case has a groove portion, and
    wherein one from among the first spiral conductive wire portion and the second spiral conductive wire portion is fitted in the groove portion.

4. The excitation coil unit according to claim 3, wherein the groove portion is configured to be parallel to the central axis of the one from among the first spiral conductive wire portion and the second spiral conductive wire portion.

* * * * *